(12) United States Patent
Wagner

(10) Patent No.: US 8,765,935 B2
(45) Date of Patent: *Jul. 1, 2014

(54) NUCLEOSIDES WITH ANTIVIRAL AND ANTICANCER ACTIVITY

(71) Applicant: Regents of the University of Minnesota, St. Paul, MN (US)

(72) Inventor: Carston R. Wagner, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/753,252

(22) Filed: Jan. 29, 2013

(65) Prior Publication Data

US 2013/0203978 A1 Aug. 8, 2013

Related U.S. Application Data

(63) Continuation of application No. 11/721,325, filed as application No. PCT/US2005/044442 on Dec. 8, 2005, now Pat. No. 8,399,428.

(60) Provisional application No. 60/634,677, filed on Dec. 9, 2004.

(51) Int. Cl.
*C07H 19/04* (2006.01)

(52) U.S. Cl.
USPC ........ 536/26.1; 536/26.7; 536/26.71; 514/43; 514/45; 514/46; 514/47

(58) Field of Classification Search
None
See application file for complete search history.

(56) References Cited

U.S. PATENT DOCUMENTS

| | | | |
|---|---|---|---|
| 5,393,877 | A | 2/1995 | McLean et al. |
| 5,543,390 | A | 8/1996 | Yatvin et al. |
| 5,614,504 | A | 3/1997 | Hadden et al. |
| 5,659,023 | A | 8/1997 | Alexander et al. |
| 5,696,097 | A | 12/1997 | Matsuda et al. |
| 6,475,985 | B1 | 11/2002 | Wagner et al. |
| 6,528,495 | B1 | 3/2003 | Uckun et al. |
| 8,399,428 | B2 | 3/2013 | Wagner |
| 2002/0004594 | A1 | 1/2002 | Borch et al. |
| 2009/0306007 | A1 | 12/2009 | Wagner |

FOREIGN PATENT DOCUMENTS

| | | |
|---|---|---|
| EP | 1827460 A1 | 9/2007 |
| WO | WO-9005736 A1 | 5/1990 |
| WO | WO-9629336 A1 | 9/1996 |
| WO | WO-9721452 A2 | 6/1997 |
| WO | WO-9949873 A1 | 10/1999 |
| WO | WO-0107454 A1 | 2/2001 |
| WO | WO-03000713 A1 | 1/2003 |
| WO | WO-2006063149 A1 | 6/2006 |

OTHER PUBLICATIONS

"U.S. Appl. No. 11/721,325, Final Office Action mailed Jul. 31, 2012", 7 pgs.

"U.S. Appl. No. 11/721,325, Non Final Office Action mailed Jan. 19, 2012", 20 pgs.

"U.S. Appl. No. 11/721,325, Notice of Allowance mailed Nov. 8, 2012", 5 pgs.

"U.S. Appl. No. 11/721,325, Preliminary Amendment filed Jun 8, 2007", 22 pgs.

"U.S. Appl. No. 11/721,325, Response filed May 21, 2012 to Non Final Office Action mailed Jan. 19, 2012", 27 pgs.

"U.S. Appl. No. 11/721,325, Response filed Oct. 31, 2012 to Final Office Action mailed Jul. 31, 2012", 20 pgs.

Abraham, Timothy W., et al., "Synthesis and Biological Activity of ARomatic Amino Acid Phosphoramidates of 5-Fluoro-2'-deoxyuridine and 1-B-Arabinofuranosylcotosine: Evidence of Phosphoramidase Activity", Journal of Medicinal Chemistry, 39(23), (Nov. 8, 1996), 4569-4575.

Balzarini, J., et al., "Antiretrovirus Specificity and Intracellular Metabolism of 2', 3'-Didehydro-2', 3'-dideoxythymidine (Stavudine) and its 5'-Monophosphate Triester Prodrug So324", Molecular Pharmacology, vol. 50, (1996), 1207-1213.

Chang, Shu-Ling, "Synthesis and Antiviral Activity of Amino Acid Carbamate Derivatives of AZT", Nucleosides, Nucleotides & Nucleic Acids, vol. 19, No. 1 & 2, (2000), 87-100.

Chou, Tsui-Fen, et al., "31P NMR and Genetic Analysis Establish hinT as the Only *Escherchia coli* Purine Nucleoside Phosphoramidase and as Essential for Growth under High Salt Conditions", The Journal of Biological Chemistry, vol. 280, No. 15, (Apr. 15, 2005), 15356-15361.

Kim, Jisook, et al., "Monitoring the Intracellular Metabolism of Nucleoside Phosphoramidate Pronucleotides by 31P NMR", Nucleosides, Nucleotides & Nucleic Acids, vol. 23, No. 1 & 2, (2004), 483-493.

Klein, Michael G., "Charaterization of PKCI and Comparative Studies with FHIT, Related Members of the HIT Protein Family", Experimental Cell Research, vol. 244, (1998), 26-32.

Mayers, Douglas L., et al., "Anti-Human Immunodeficiency Virus 1 (HIV-1) Activities of 3-deazaadenosine analogs: Increased Potency Against 3'-azido-3'-deoxythymidine-resistant HIV-1 Strains", Proc. Natl. Acad. Sci., vol. 92, (Jan. 1995), 215-219.

McGuigan, Christopher, et al., "Intracellular Delivery of Bioactive AZT Nucleotides by Aryl Phosphate Derivatives of AZT", J. Med. Chem., 36, (1993), pp. 1048-1052.

(Continued)

*Primary Examiner* — Patrick Lewis
(74) *Attorney, Agent, or Firm* — Schwegman Lundberg & Woessner, P.A.

(57) ABSTRACT

The invention provides a compound of formula (I), wherein R1-R6 and X have any of the values described, as well as pharmaceutical compositions comprising such compounds and therapeutic methods comprising the administration of such compounds.

16 Claims, 4 Drawing Sheets

(56) References Cited

OTHER PUBLICATIONS

McGuigan, Christopher, et al., "Kinase Bypass: A New Strategy for Anti-HIV Drug Design", Bioorganic & Medicinal Chemistry Letters, vol. 3, No. 6, (1993), 1207-1210.

McIntee, Edward J., et al., "Probing the Mechanism of Action and Decomposition of Amino Acid Phosphomonoester Amidates of Antiviral Nucleoside Prodrugs", J. Med. Chem., 40, (1997), pp. 3323-3331.

Montgomery, John A, et al., "A Comparison of Two Methods for the Preparation of 3-Deazapurine Ribonucleosides", J. Heterocyclic Chem, vol. 14, (1977), 195.

Montgomery, John A, et al., "Carbocyclic Analogue of 3-Deazaadenosine: A Novel Antiviral Agent using S-Adenosylhomocysteine Hyrdolase as a Pharmacological Target", J. Med. Chem., vol. 25, (1982), 626-629.

Wagner, Carston R, et al., "Aromatic Amino Acid Phosphoramidate DI- and Triesters of 3'-Azido-3'-Deoxythymidine (AZT) are Non-Toxic Inhibitors of HIV-1 Replication", Bioorganic & Medicinal Chemistry Letters, vol. 5, No. 16, (1995), 1819-1824.

"European Application Serial No. 05853381.1, Supplementary European Search Report mailed Feb. 9, 2012", 10 pgs.

"International Application Serial No. PCT/US2005/044442, International Preliminary Report on Patentability mailed Jun. 13, 2007", 4 pgs.

"International Application Serial No. PCT/US2005/044442, International Search Report mailed May 10, 2006", 2 pgs.

"International Application Serial No. PCT/US2005/044442, Written Opinion mailed May 10, 2006", 3 pgs.

| Compound | R | R' | X | * |
|---|---|---|---|---|
| 5 | methoxy | benzyl | O | (S) |
| 6 | methoxy | 3-indolylmethyl | O | (S) |
| 7 | methoxy | benzyl | CH$_2$ | (S) |
| 14 | methylamino | benzyl | O | (S) |
| 16 | methylamino | 3-indolylmethyl | O | (S) |

NUCLEOSIDES WITH ANTIVIRAL AND ANTICANCER ACTIVITY

CROSS-REFERENCE TO RELATED APPLICATIONS

This application is a continuation of U.S. patent application Ser. No. 11/721,325, filed Aug. 18, 2009, which is a U.S. National Stage Application Under 35 U.S.C. 371 from International Application No. PCT/US2005/044442, filed Dec. 8, 2005 and published as WO 2006/063149 on Jun. 15, 2006 which claims priority to U.S. Provisional Application Ser. No. 60/634,677, filed on Dec. 9, 2004, which applications are incorporated by reference herein.

GOVERNMENT FUNDING

The invention described herein was made with U.S. Government support under grant CA 89615 awarded by the National Institutes of Health, National Cancer Institute. The United States Government has certain rights in the invention.

BACKGROUND OF THE INVENTION

Histidine triad enzymes are a superfamily of relatively small (MW 28-34 Kda), homodimeric nucleoside monophosphate hydrolases and transferases containing an active site motif related to His-X-His-X-His-X-X, where X is a hydrophobic amino acid (Bieganowski, P., et al., *J. Biol. Chem.*, 2002, 277, 10852-10860). The HINT branch is the most ancient branch, having representatives in all forms of life (Bieganowski, P., et al., *J. Biol. Chem.*, 2002, 277, 10852-10860; and Brenner, C., et al., *Nature Struc. Biol.*, 1997, 4, 231-238).

The signature histidine triad residues were shown to be largely responsible for stabilizing binding to the phosphates, while the base appeared to be sandwiched between two phenylalanines and an isoleucine (Brenner, C., et al., *Nature Struc. Biol.*, 1997, 4, 231-238; and Lima, C. D., et al., *Science*, 1997, 278, 286-290). Further inspection revealed that N-7 and O-4 for guanosine and N-7 and N-4 for adenosine are almost completely solvent exposed, while little, if any, specific binding interactions surrounding N-2 and N-3 were observed. Hydrogen bonding interactions were observed between Asp-43 and both of the 2'- and 3'-hydroxyl groups, which is consistent with the reduced ability of 2'-deoxy nucleoside phosphoramidates to serve as substrates.

Although HINTs have been associated only recently with adenosine phosphoramidase activity, nucleoside phosphoramidase activity has been observed in partially purified extracts from rabbit liver, whole cells and extracts of the human T-leukemia, CEM cells, peripheral blood mononuclear cells (PBMCs) and green monkey Vero cells (Ledneva, R. K., et al., 1970, *Dokl. Akad. Nauk Sssr* 193, 1308-10; Dudkin, S. M., et al., 1971, *Febs* 16, 48-50; Abraham, T. W., et al., 1996, *J. Med. Chem.* 39, 4569-4575; Abraham, T. W., et al., 1997, *Nucleosides Nucleotides* 16, 2079-2092; Chang, S.-L., et al., 2001, *J. Med. Chem.* 44, 223-231).

U.S. Pat. No. 6,475,985 reports certain specific nucleoside phosphoramidate analogs having anticancer and/or antiviral properties. There continues to be an interest in phosphoramidate nucleoside analogs due to their demonstrated utility as prodrugs of antiviral and anticancer nucleoside monophosphates, or pronucleotides (McGuigan, C., et al., 1993, *Bioorg. Med. Chem. Lett.* 3, 1207-1210; Balzarini, J., et al., 1996, *Mol. Pharmacol.* 50, 1207-1213; Chang, S. L., et al., 2000, *Nucleosides, Nucleotides & Nucleic Acids* 19, 87-100; Kim, J., Drontle, et al., 2004, *Nucleos. Nucleot. Nucleic Acids* 23, 483-493; and Klein, M. G., et al., 1998, *Exp. Cell. Res.* 244, 26-32).

In spite of the above reports, there is currently a need for chemotherapeutic agents with antiviral and or anticancer properties. In particular there is a need for agents that are selectively activated at the sight of a disease or virus.

SUMMARY OF THE INVENTION

Although, the nature of the enzyme responsible for phosphoramidate hydrolysis has not been determined, direct evidence of intracellular P—N bond hydrolysis by a putative phosphoramidase was demonstrated by studies of the intracellular metabolism of fluorodeoxyuridine phosphoramidates with permeablized cells and $O^{18}$ labeled AZT tryptophan methyl ester phosphoramidate with capillary LC-ESI-MS/MS.

Recently, hHINT1 has been isolated and cloned by a combination of affinity chromatography and T7 phage display a human phosphoramidase. Early studies have demonstrated that the enzyme will efficiently hydrolyze guanosine, adenosine and to a limited extent uridine and cytosine phosphoramidates containing primary amines. hHINT1 has been shown to be over-expressed in breast, lung and ovarian cancer tissues relative to normal tissues. Recently, it has been shown that human breast cancer has at least 6-times more expressed hHINT1 activity than normal breast tissues. In addition, it is known that the hHINT1 is overexpressed in the liver and brain. Consequently, antiviral or anticancer phosphoramidates that are substrates for hHINTs should facilitate the design of tissue specific antiviral and anticancer phosphoramidate based therapeutics.

Inspection of the active site of hHINT1 has revealed that hydrogen bonding, ion pairing or polar interactions at the 2'- and 3'-positions preferentially interact with the active site residue Asp-43, which is consistent with the reduced ability of 2'-deoxy nucleoside phosphoramidates to serve as substrates. In addition, phosphoramidates with a D-amino acid are hydrolyzed at least 20-fold more efficiently than phosphoramidates containing L-amino acids. Consequently, compounds containing 1) an electropositive group at the 2'-position, and/or 2) a group having a stereochemistry that corresponds to that of an N-linked D-amino acid on the phosphorous are especially good substrates for hHINT1.

The present invention provides compounds that act as antiviral and or anticancer agents. Accordingly there is provided a compound of the invention which is a compound of formula I:

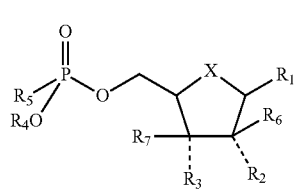

wherein:

$R_1$ is adenine, guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1\text{-}C_6)$alkanoyloxy, trifluoromethyl, hydroxy$(C_1\text{-}C_6)$alkyl, $-(CH_2)_{1-4}P(=O)(OR_w)_2$ aryl, aryl$(C_1\text{-}C_6)$alkyl, or $NR_xR_y$;

$R_2$ and $R_6$ are each independently hydrogen, halo, hydroxy, $(C_1\text{-}C_6)$alkyl, $(C_3\text{-}C_6)$cycloalkyl, $(C_1\text{-}C_6)$alkoxy, $(C_3\text{-}C_6)$cycloalkyloxy, $(C_1\text{-}C_6)$alkanoyl, $(C_1\text{-}C_6)$alkanoyloxy, trifluoromethyl, azido, cyano, $-N(R_z)C(=O)N(R_{aa})(R_{ab})$, $-N(R_z)C(=O)OR_{ac}$, or $NR_{ad}R_{ae}$, provided that one of $R_2$ and $R_6$ is hydroxy halo, $(C_1\text{-}C_6)$alkoxy, $(C_3\text{-}C_6)$cycloalkyloxy, trifluoromethyl, cyano, or $NR_{ad}R_{ae}$;

$R_3$ is hydrogen, halo, hydroxy, $(C_1\text{-}C_6)$alkyl, $(C_3\text{-}C_6)$cycloalkyl, $(C_1\text{-}C_6)$alkoxy, $(C_3\text{-}C_6)$cycloalkyloxy, $(C_1\text{-}C_6)$alkanoyl, $(C_1\text{-}C_6)$alkanoyloxy, trifluoromethyl, azido, cyano, $-N(R_z)C(=O)N(R_{aa})(R_{ab})$, $-N(R_z)C(=O)OR_{ac}$, or $NR_{ad}R_{ae}$;

$R_4$ is hydrogen, $(C_1\text{-}C_6)$alkyl, $(C_3\text{-}C_6)$cycloalkyl, aryl, aryl$(C_1\text{-}C_6)$alkyl, or 2-cyanoethyl;

$R_5$ is an amino acid, a peptide, or $NR_aR_b$;

$R_7$ is hydrogen, halo, hydroxy, $(C_1\text{-}C_6)$alkyl, $(C_3\text{-}C_6)$cycloalkyl, $(C_1\text{-}C_6)$alkoxy, $(C_3\text{-}C_6)$cycloalkyloxy, $(C_1\text{-}C_6)$alkanoyl, $(C_1\text{-}C_6)$alkanoyloxy, trifluoromethyl, azido, cyano, $-N(R_z)C(=O)N(R_{aa})(R_{ab})$, $-N(R_z)C(=O)OR_{ac}$, or $NR_{ad}R_{ae}$;

X is oxy, thio, or methylene;

each $R_a$ and $R_b$ is independently hydrogen, $(C_1\text{-}C_6)$alkyl, $(C_3\text{-}C_6)$cycloalkyl, aryl, or Het; or $R_a$ and $R_b$ together with the nitrogen to which they are attached form a nitrogen-linked Het;

each $R_w$ is independently hydrogen or $(C_1\text{-}C_6)$alkyl;

$R_x$ and $R_y$ are each independently hydrogen, $(C_1\text{-}C_6)$alkyl, $(C_3\text{-}C_6)$cycloalkyl, phenyl, benzyl, phenethyl, or $(C_1\text{-}C_6)$alkanoyl; or $R_x$ and $R_y$ together with the nitrogen to which they are attached are pyrrolidino, piperidino or morpholino;

$R_z$ is hydrogen, $(C_1\text{-}C_6)$alkyl, $(C_3\text{-}C_6)$cycloalkyl, phenyl, benzyl, or phenethyl;

$R_{aa}$ and $R_{ab}$ are each independently hydrogen, $(C_1\text{-}C_6)$alkyl, $(C_3\text{-}C_6)$cycloalkyl, phenyl, benzyl, or phenethyl; or $R_{aa}$ and $R_{ab}$ together with the nitrogen to which they are attached are pyrrolidino, piperidino or morpholino;

$R_{ac}$ is hydrogen, $(C_1\text{-}C_6)$alkyl, $(C_3\text{-}C_6)$cycloalkyl, phenyl, benzyl, or phenethyl;

$R_{ad}$ is hydrogen $(C_1\text{-}C_6)$alkyl, $(C_3\text{-}C_6)$cycloalkyl, phenyl, benzyl, or phenethyl;

$R_{ae}$ is hydrogen, $(C_1\text{-}C_6)$alkyl, $(C_3\text{-}C_6)$cycloalkyl, phenyl, benzyl, or phenethyl;

wherein any $(C_1\text{-}C_6)$alkyl of $R_1\text{-}R_7$, $R_a$, $R_b$, $R_w$, $R_x$, $R_y$, $R_z$, $R_{aa}$, $R_{ab}$, $R_{ac}$, $R_{ad}$, and $R_{ae}$ is optionally substituted with one or more (e.g. 1, 2, 3, or 4) halo, hydroxy, $(C_1\text{-}C_6)$alkoxy, $(C_3\text{-}C_6)$cycloalkyloxy, $(C_1\text{-}C_6)$alkanoyl, $(C_1\text{-}C_6)$alkanoyloxy, trifluoromethyl, azido, cyano, oxo $(=O)$, $(C_1\text{-}C_6)$alkyl, $(C_3\text{-}C_6)$cycloalkyl, $(C_3\text{-}C_6)$cycloalkyl$(C_1\text{-}C_6)$alkyl, $(C_1\text{-}C_6)$alkyl-S-$(C_1\text{-}C_6)$alkyl-, aryl, Het, aryl$(C_1\text{-}C_6)$alkyl, or Het$(C_1\text{-}C_6)$alkyl, or $NR_{aj}R_{ak}$; wherein each $R_{aj}$ and $R_{ak}$ is independently hydrogen, $(C_1\text{-}C_6)$alkyl, $(C_3\text{-}C_6)$cycloalkyl, phenyl, benzyl, or phenethyl;

and wherein any aryl or Het may optionally be substituted with one or more substituents selected from the group consisting of halo, hydroxy, $(C_1\text{-}C_6)$alkyl, $(C_3\text{-}C_6)$cycloalkyl, $(C_1\text{-}C_6)$alkoxy, $(C_3\text{-}C_6)$cycloalkyloxy, $(C_1\text{-}C_6)$alkanoyl, $(C_1\text{-}C_6)$alkanoyloxy, trifluoromethyl, trifluoromethoxy, nitro, cyano, and amino;

or a pharmaceutically acceptable salt thereof. In one embodiment the invention provides a compound of formula (I); provided that $R_2$ and $R_3$ are each not hydroxy when $R_1$ is adenine, guanine, cytosine, thymine, or uracil, X is oxy, $R_5$ is an amino acid or a peptide; $R_6$ is hydrogen, and $R_7$ is hydrogen; and; provided $R_1$ is not 3-deazaadenine, when $R_2$ is hydroxy; $R_3$ is hydroxy; $R_4$ is hydrogen; $R_5$ a nitrogen linked radical of formula III;

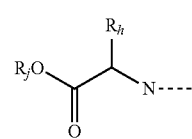

wherein $R_h$ is benzyl or 3-indolylmethyl; and $R_j$ is methyl; x is oxy, $R_6$ is hydrogen, and $R_7$ is hydrogen.

The invention also provides a method for treating a viral infection in an animal comprising administering an effective amount of a compound of formula I or a pharmaceutically acceptable salt thereof to an animal (e.g. a mammal) in need of such treatment.

The invention also provides a method for treating HCV in an animal comprising administering an effective amount of a compound of formula I or a pharmaceutically acceptable salt thereof to an animal in need of such treatment.

The invention also provides a method for treating a metabolic liver disorder (e.g. hemochromatosis, cirrhosis, Wilson's disease, biliary atresia, hepatitis, or any other genetic or environmentally induced liver disease) in an animal comprising administering an effective amount of a compound of formula I or a pharmaceutically acceptable salt thereof to an animal in need of such treatment.

The invention also provides a method for treating a cancer in the liver of an animal comprising administering an effective amount of a compound of formula I or a pharmaceutically acceptable salt thereof to an animal in need of such treatment.

The invention also provides a method for treating cancer in the brain of an animal comprising administering an effective amount of a compound of formula I or a pharmaceutically acceptable salt thereof to an animal in need of such treatment.

The invention also provides a method for treating breast cancer, lung cancer or ovarian cancer in an animal comprising administering an effective amount of a compound of formula I or a pharmaceutically acceptable salt thereof to an animal in need of such treatment.

The invention also provides the use of a compound of formula I or a pharmaceutically acceptable salt thereof to prepare a medicament for treating a viral infection in a mammal.

The invention also provides the use of a compound of formula I or a pharmaceutically acceptable salt thereof to prepare a medicament for treating HCV in a mammal.

The invention also provides the use of a compound of formula I or a pharmaceutically acceptable salt thereof to prepare a medicament for treating a metabolic liver disorder in a mammal.

The invention also provides the use of a compound of formula I or a pharmaceutically acceptable salt thereof to prepare a medicament for treating a cancer in the liver of a mammal.

The invention also provides the use of a compound of formula I or a pharmaceutically acceptable salt thereof to prepare a medicament for treating cancer in the brain of a mammal.

The invention also provides the use of a compound of formula I or a pharmaceutically acceptable salt thereof to prepare a medicament useful for treating breast cancer, lung cancer or ovarian cancer in a mammal.

DETAILED DESCRIPTION

Figure 1:
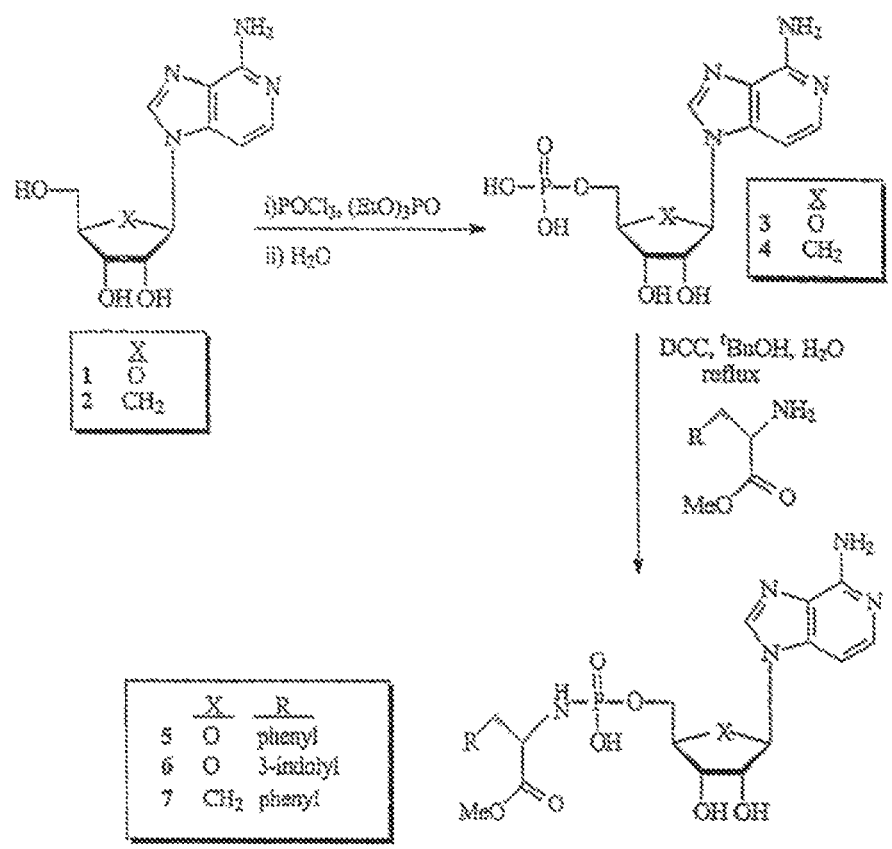
FIG. 1 Illustrates the synthesis of representative compounds of the invention.
Figure 2:
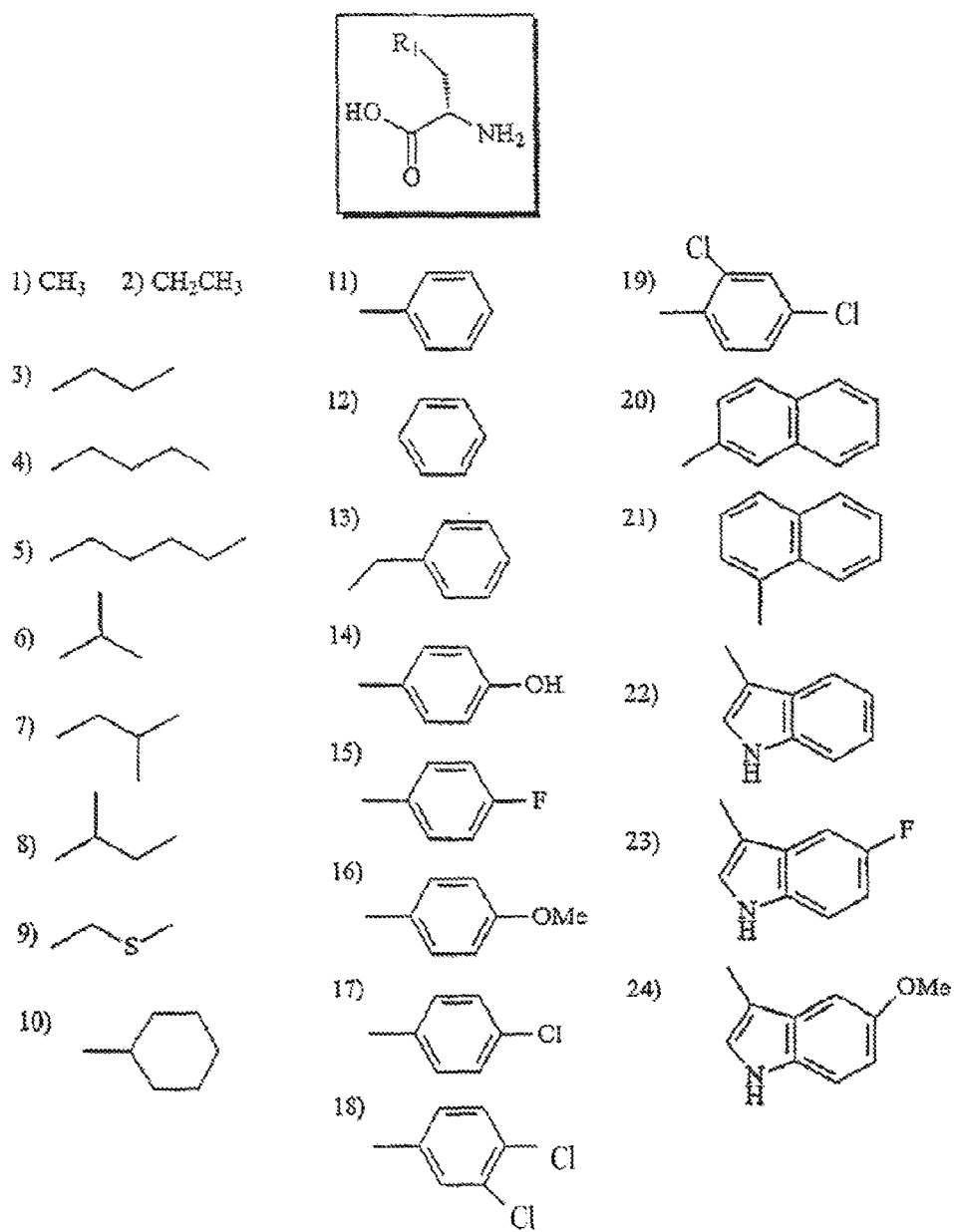
FIG. 2 Illustrates starting materials useful for preparing compounds of the invention.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het encompasses a radical of a monocyclic, bicyclic, or tricyclic ring system containing a total of 3-20 atoms, including one or more (e.g., 1, 2, 3, 4, 5, or 6) carbon atoms, and one or more (e.g., 1, 2, 3, or 4) heteroatoms selected from oxygen, sulfur, and N(X) wherein X is absent or is H, O, $(C_1-C_4)$alkyl, phenyl or benzyl, wherein one or more ring carbons of Het can optionally be substituted with oxo (=O); Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. The term Het encompasses Heteroaryl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids protected at the carboxy terminus (e.g. as a $(C_1-C_6)$alkyl, phenyl or benzyl ester or as an amide, such asfor example, a mono-$(C_1-C_6)$alkyl or di-$(C_1-C_6)$alkyl amide. Other suitable carboxy protecting groups are known to those skilled in the art (See for example, T. W. Greene, *Protecting Groups In Organic Synthesis*; Wiley: New York, 1981, and references cited therein). An amino acid can be linked to the remainder of a compound of the invention through the carboxy terminus, the amino terminus, or through any other convenient point of attachment. Preferably, when $R_5$ is an amino acid, the amino acid is linked to phosphorous through the amino nitrogen, forming a phosphoramidate. The term animal includes birds, reptiles and mammals. In one specific embodiment of the invention the animal is a human.

The term "peptide" describes a sequence of 2 to 25 amino acids (e.g. as defined hereinabove) or peptidyl residues. The sequence may be linear or cyclic. A peptide can be linked to the remainder of a compound of formula I through the carboxy terminus, the amino terminus, or through any other convenient point of attachment. Preferably a peptide comprises 2 to 25, or 5 to 20 amino acids. Peptide derivatives can be prepared using techniques that are well known in the art, for example, using solid phase peptide synthesis techniques. In one embodiment, when $R_5$ is a peptide, the peptide is linked to phosphorous through the N-terminal nitrogen, forming a phosphoramidate. In another embodiment, when $R_5$ is a peptide, the peptide is linked to phosphorous through the N-terminal nitrogen, forming a phosphoramidate, and the carbon adjacent to the N-terminal nitrogen has the configuration of a D-amino acid.

The term "viral infection" includes human immunodeficiency virus (HIV), herpes simplex virus-2 (HSV-2), varicellazoster, vaccinia, human cytomegalovirus, ebola, hepatitis B (HBV), hepatitis C (HCV) and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_a$ is $(C_1-C_6)$alkyl optionally substituted with one or more halo, hydroxy, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, Het, aryl$(C_1-C_6)$alkyl, or Het$(C_1-C_6)$alkyl, or $NR_{aj}R_{ak}$; wherein each $R_{aj}$ and $R_{ak}$ is independently hydrogen, $(C_1-C_6)$alkyl, $(C_3-C_6)$cycloalkyl, phenyl, benzyl, or phenethyl.

A specific value for $R_a$ is $(C_1-C_6)$alkyl optionally substituted with one or more halo, hydroxy, $(C_1-C_6)$alkoxy, $(C_1-C_6)$alkanoyl, $(C_1-C_6)$alkanoyloxy, trifluoromethyl, cyano, aryl, or Het.

A specific value for $R_a$ is $(C_1-C_6)$alkyl optionally substituted with one or more aryl or Het.

A specific value for $R_a$ is $(C_1-C_6)$alkyl substituted with a phenyl, naphthyl, pyridyl, indolyl, isoindolyl, furyl, thienyl, pyrrolyl, benzofuranyl, benzothienyl, imidazolyl, thiazoyl, pyrrolidinyl, piperidinyl, piperazinyl, or morpholino ring, which ring is optionally substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino.

A specific value for $R_a$ is $(C_1-C_6)$alkyl substituted with a phenyl or indolyl ring, which ring is optionally substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino.

A specific value for $R_a$ is $(C_1-C_6)$alkyl substituted with a phenyl ring.

A specific value for $R_a$ is $(C_1-C_6)$alkyl substituted with an indolyl ring.

A specific value for $R_a$ is phenylmethyl, phenethyl, indolylmethyl, or 2-indolylethyl.

A specific value for $R_a$ is 2-indol-3-ylethyl.

A specific value for $R_b$ is hydrogen.

A specific compound of formula (I) has the formula $R_5$-B, wherein B is a phosphorous-linked 9-beta-D-arabinofuranosyladenosine monophosphate, 9-beta-D-arabinofuranosylguanosine monophosphate, or 9-beta-D-arabinofuranosylcytosine monophosphate and wherein $R_5$ has any of the values defined herein.

A specific value for $R_5$ is $NR_aR_b$ wherein $R_a$ is 2-indol-3-ylethyl; and $R_b$ is hydrogen.

A specific value for $R_1$ is guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$ aryl, aryl$(C_1-C_6)$alkyl, or $NR_xR_y$.

A specific value for $R_1$ is adenine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$ aryl, aryl$(C_1-C_6)$alkyl, or $NR_xR_y$.

A specific value for $R_1$ is adenine, guanine, cytosine, thymine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$ aryl, aryl$(C_1-C_6)$alkyl, or $NrxRy$.

A specific value for $R_1$ is cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$ aryl, aryl$(C_1-C_6)$alkyl, or $NrxRy$.

A specific value for $R_1$ is 3-deazaadenine optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$ aryl, aryl$(C_1-C_6)$alkyl, or $NR_xR_y$.

A specific value for $R_1$ is adenine, guanine, cytosine, thymine, 3-deazaadenine, or uracil.

A specific value for $R_1$ is guanine, cytosine, thymine, 3-deazaadenine, or uracil.

A specific value for $R_1$ is cytosine, thymine, 3-deazaadenine, or uracil.

A specific value for $R_1$ is cytosine, thymine, or uracil.

A specific value for $R_1$ is a nitrogen linked radical of formula VI:

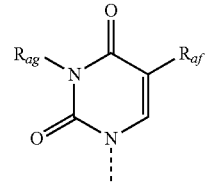

VI wherein $R_{af}$ is hydrogen, halo, $(C_1-C_6)$alkyl, $(C_3-C_6)$cycloalkyl, or trifluoromethyl; and $R_{ag}$ is hydrogen, $(C_1-C_6)$alkyl, $(C_3-C_6)$cycloalkyl, trifluoromethyl, hydroxy$(C_1-C_6)$alkyl, or $-(CH_2)_{1-4}P(=O)(OR_w)_2$.

A specific value for $R_2$ is hydroxy.
A specific value for $R_2$ is halo.
A specific value for $R_2$ is fluoro.
A specific value for $R_2$ is chloro.
A specific value for $R_2$ is $(C_1-C_6)$alkoxy.
A specific value for $R_2$ is methoxy.
A specific value for $R_2$ trifluoromethyl.
A specific value for $R_2$ is cyano.
A specific value for $R_2$ is amino, methylamino, dimethylamino, ethylamino, or dimethylamino.
A specific value for $R_3$ is hydroxy.
A specific value for $R_3$ is hydrogen.
A specific value for $R_3$ is halo.
A specific value for $R_3$ is fluoro.
A specific value for $R_3$ is chloro.
A specific value for $R_3$ is trifluoromethyl.
A specific value for $R_3$ is azido
A specific value for $R_3$ is cyano.
A specific value for $R_3$ is amino, methylamino, dimethylamino, ethylamino, or dimethylamino.
A specific value for $R_4$ is hydrogen.
A specific value for $R_4$ is methyl or ethyl.
A specific value for $R_4$ is 2-cyanoethyl.
A specific value for $R_5$ is an amino acid.
A specific value for $R_5$ is a peptide.
A specific value for $R_5$ is a nitrogen linked radical of formula II:

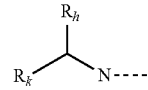

II wherein:

$R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z;

each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino; and $R_k$ is hydrogen or $(C_1-C_5)$alkyl that is optionally substituted with one or more (e.g. 1, 2, 3, or 4) halo, hydroxy, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, oxo (=O) or $NR_{ad}R_{ae}$. A specific value for $R_k$ is $(C_1-C_5)$alkyl optionally substituted with one or more (e.g. 1, 2, 3, or 4) halo, hydroxy, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, oxo (=O) or $NR_{ad}R_{ae}$.

A specific value for $R_h$ is hydrogen, $(C_1-C_6)$alkyl, phenylmethyl, or 3-indolylmethyl.

A specific value for $R_h$ is phenylmethyl.

A specific value for $R_h$ is 3-indolylmethyl.

A specific compound is a compound wherein the carbon bearing $R_h$ has the (R) absolute configuration.

A specific value for $R_5$ is a nitrogen linked radical of formula III:

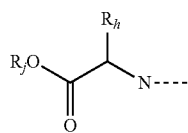

III wherein $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_j$ is hydrogen, $(C_1-C_6)$alkyl, phenyl, benzyl, or phenethyl; and wherein each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

A specific value for $R_h$ is hydrogen, $(C_1-C_6)$alkyl, phenylmethyl, or 3-indolylmethyl.

A specific value for $R_h$ is phenylmethyl.

A specific value for $R_h$ is 3-indolylmethyl.

A specific value for $R_6$ is hydrogen or $(C_1-C_6)$alkyl.

A specific value for $R_2$ is hydrogen or alkyl; and $R_6$ is halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N($R_z$)C(=O)N($R_{aa}$)($R_{ab}$), —N($R_z$)C(=O)O$R_{ac}$, or $NR_{ad}R_{ae}$.

A specific value for $R_7$ is hydrogen or $(C_1-C_6)$alkyl.

A specific compound is a compound wherein $R_3$ is hydrogen or alkyl; and $R_7$ is halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N($R_z$)C(=O)N($R_{aa}$)($R_{ab}$), —N($R_z$)C(=O)O$R_{ac}$, or $NR_{ad}R_{ae}$;

A specific compound is (2-(3-indolyl)-1(R)-methylcarbamoylethyl)-phosphoramidic acid mono(1-B-arabinofuranosyladenosine)ester; or a pharmaceutically acceptable salt thereof.

In one specific embodiment the invention provides a compound of formula I:

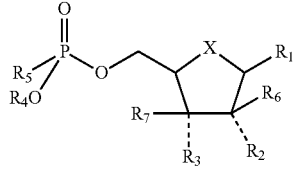

I wherein:

$R_1$ is adenine, guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}$P(=O)(O$R_w$)$_2$ aryl, aryl$(C_1-C_6)$alkyl, or $NR_xR_y$;

$R_2$ and $R_6$ are each independently hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N($R_z$)C(=O)N($R_{aa}$)($R_{ab}$), —N($R_z$)C(=O)O$R_{ac}$, or $NR_{ad}R_{ae}$, provided that one of $R_2$ and $R_6$ is hydroxy halo, $(C_1-C_6)$alkoxy, $(C_3-C_6)$cycloalkyloxy, trifluoromethyl, cyano, or $NR_{ad}R_{ae}$;

$R_3$ is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N($R_z$)C(=O)N($R_{aa}$)($R_{ab}$), —N($R_z$)C(=O)O$R_{ac}$, or $NR_{ad}R_{ae}$;

$R_4$ is hydrogen, $(C_1-C_6)$alkyl, $(C_3-C_6)$cycloalkyl, aryl, aryl$(C_1-C_6)$alkyl, or 2-cyanoethyl;

$R_5$ is $NR_aR_b$;

$R_7$ is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N($R_z$)C(=O)N($R_{aa}$)($R_{ab}$), —N($R_z$)C(=O)O$R_{ac}$, or $NR_{ad}R_{ae}$;

X is oxy, thio, or methylene;

each $R_a$ and $R_b$ is independently hydrogen, $(C_1-C_6)$alkyl, $(C_3-C_6)$cycloalkyl, aryl, or Het; or $R_a$ and $R_b$ together with the nitrogen to which they are attached form a nitrogen-linked Het;

each $R_w$ is independently hydrogen or $(C_1-C_6)$alkyl;

$R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperidino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino;

$R_{ac}$ is hydrogen, $(C_1-C_6)$alkyl, $(C_3-C_6)$cycloalkyl, phenyl, benzyl, or phenethyl;

$R_{ad}$ is hydrogen $(C_1-C_6)$alkyl, $(C_3-C_6)$cycloalkyl, phenyl, benzyl, or phenethyl;

$R_{ae}$ is hydrogen, $(C_1-C_6)$alkyl, $(C_3-C_6)$cycloalkyl, phenyl, benzyl, or phenethyl;

wherein any $(C_1-C_6)$alkyl of $R_1$-$R_7$, $R_a$, $R_b$, $R_w$, $R_x$, $R_y$, $R_z$, $R_{aa}$, $R_{ab}$, $R_{ac}$, $R_{ad}$, and $R_{ae}$ is optionally substituted with one or more (e.g. 1, 2, 3, or 4) halo, hydroxy, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, oxo (=O), $(C_1-C_6)$alkyl, $(C_3-C_6)$cycloalkyl, $(C_3-C_6)$cycloalkyl$(C_1-C_6)$alkyl, $(C_3-C_6)$alkyl-S—$(C_1-C_6)$alkyl-, aryl, Het, aryl$(C_1-C_6)$alkyl, or Het$(C_1-C_6)$alkyl, or $NR_{aj}R_{ak}$; wherein each $R_{aj}$ and $R_{ak}$; is independently hydrogen, $(C_1-C_6)$alkyl, $(C_3-C_6)$cycloalkyl, phenyl, benzyl, or phenethyl;

and wherein any aryl or Het may optionally be substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino;

or a pharmaceutically acceptable salt thereof.

In one specific embodiment the invention provides a compound of formula I:

wherein:

$R_1$ is adenine, guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)(OR_w)_2$ aryl, aryl$(C_1-C_6)$alkyl, or $NR_xR_y$;

$R_2$ and $R_6$ are each independently hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$, provided that one of $R_2$ and $R_6$ is hydroxy halo, $(C_1-C_6)$alkoxy, $(C_3-C_6)$cycloalkyloxy, trifluoromethyl, cyano, or $NR_{ad}R_{ae}$;

$R_3$ is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$;

$R_4$ is hydrogen, $(C_1-C_6)$alkyl, $(C_3-C_6)$cycloalkyl, aryl, aryl$(C_1-C_6)$alkyl, or 2-cyanoethyl;

$R_5$ is an amino acid, a peptide, or $NR_aR_b$;

$R_7$ is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$;

X is oxy, thio, or methylene;

each $R_a$ and $R_b$ is independently hydrogen, $(C_1-C_6)$alkyl, $(C_3-C_6)$cycloalkyl, aryl, or aryl$(C_1-C_6)$alkyl; or $R_a$ and $R_b$ together with the nitrogen to which they are attached form a pyrrolidino, piperidino or morpholino;

each $R_w$ is independently hydrogen or $(C_1-C_6)$alkyl;

$R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperidino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino;

$R_{ac}$ is hydrogen, $(C_1-C_6)$alkyl, $(C_3-C_6)$cycloalkyl, phenyl, benzyl, or phenethyl;

$R_{ad}$ is hydrogen $(C_1-C_6)$alkyl, $(C_3-C_6)$cycloalkyl, phenyl, benzyl, or phenethyl;

$R_{ae}$ is hydrogen, $(C_1-C_6)$alkyl, $(C_3-C_6)$cycloalkyl, phenyl, benzyl, or phenethyl;

wherein any $(C_1-C_6)$alkyl of $R_1$-$R_7$, $R_a$, $R_b$, $R_w$, $R_x$, $R_y$, $R_z$, $R_{aa}$, $R_{ab}$, $R_{ac}$, $R_{ad}$, and $R_{ae}$ is optionally substituted with one or more (e.g. 1, 2, 3, or 4) halo, hydroxy, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, oxo (=O), $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl, or $NR_{aj}R_{ak}$; wherein each $R_{aj}$ and $R_{ak}$ is independently hydrogen, $(C_1-C_6)$alkyl, $(C_3-C_6)$cycloalkyl, phenyl, benzyl, or phenethyl;

and wherein any aryl or heteroaryl may optionally be substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino;

or a pharmaceutically acceptable salt thereof;

provided that $R_2$ and $R_3$ are each not hydroxy when $R_1$ is adenine, guanine, cytosine, thymine, or uracil, X is oxy, $R_6$ is hydrogen, and $R_7$ is hydrogen; and; provided $R_1$ is not 3-deazaadenine, when $R_2$ is hydroxy; $R_3$ is hydroxy; $R_4$ is hydrogen; $R_5$ a nitrogen linked radical of formula III;

wherein $R_h$ is benzyl or 3-indolylmethyl; and $R_j$ is methyl; x is oxy, $R_6$ is hydrogen, and $R_7$ is hydrogen.

Processes for preparing compounds of formula I are provided as further embodiments of the invention and are illustrated by the following procedures in which the meanings of the generic radicals are as given above unless otherwise qualified.

Figure 4:
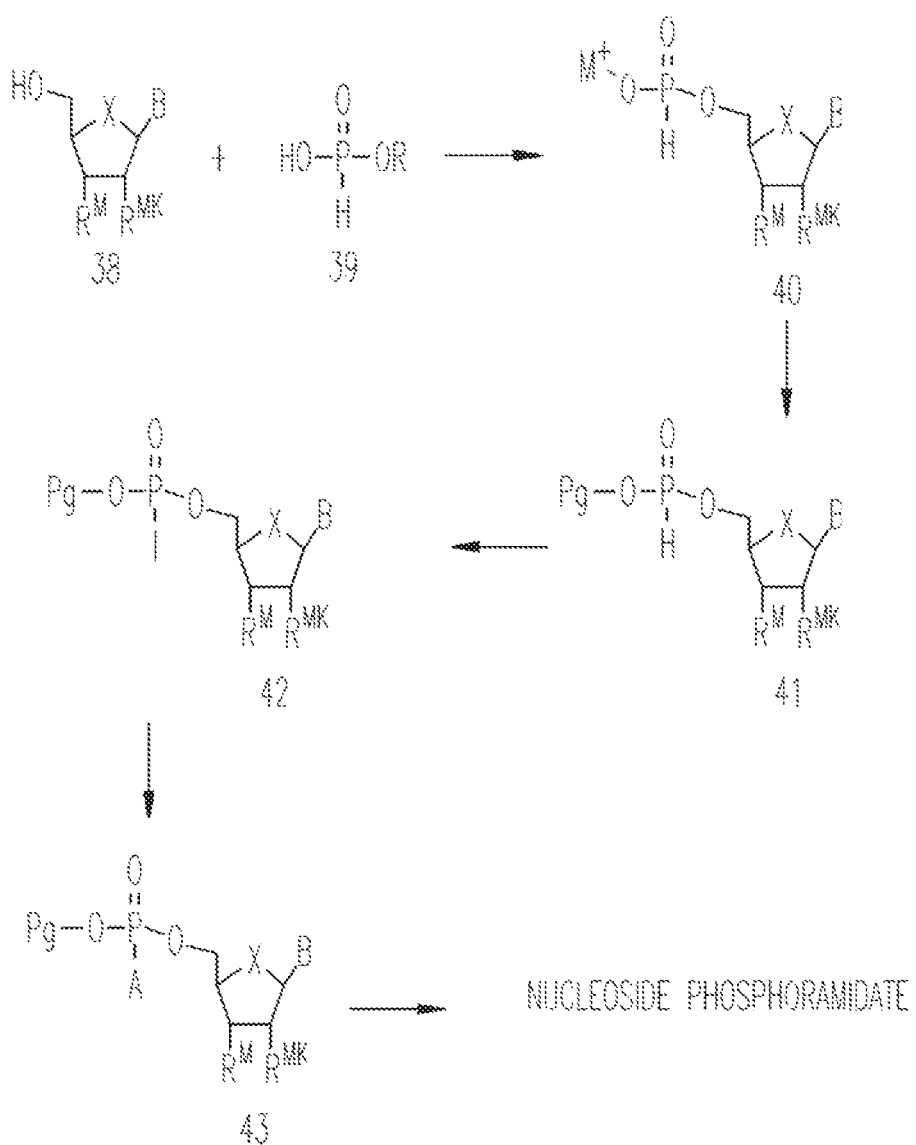
FIG. 4 Illustrates the preparation of compounds of the invention.

As illustrated in FIG. 4, a compound of formula I can be prepared from a corresponding compound of formula 43 by removal of the hydroxy protecting group "pg" (e.g. a silyl protecting group such as a trimethylsilyl group).

The preparation of amino acid phosphoramidates of 3-deaza adenosine and 3-deaza aristeromycin is shown in FIG. 1. Direct phosphorylation of DZA and DZAri can be accomplished using phosphorus oxychloride in triethylphosphate, yielding the monophosphates 3 and 4 in 81% and 67%, respectively (Yoshikawa et al., *Tetrahedron Lett.*, 50:5065-5068 (1967); Yoshikawa et al., *Bull. Chem. Soc. Jpn.*, 42:3505-3508 (1969)). Construction of the phosphoramidates was based on a procedure by Moffatt and Khorana, in which they describe the dicyclohexylcarbodiimide (DCC)-mediated coupling of adenosine 5'-monophosphate to p-anisidine (Moffatt et al., *J. Am. Chem. Soc.*, 83:649-658 (1961)). The monophosphates (3 and 4) were then coupled with DCC in refluxing tert-BuOH/H$_2$O to the carbomethoxy esters of L-phenylalanine and L-tryptophan. The crude product mixtures were purified by reverse phase HPLC on a C8 semi-prep column, to give 5-7 in a yield of 8-30%.

As illustrated in FIG. 4, reaction of a nucleoside of formula 38, wherein B is any suitable nucleoside base and R″ and R‴ are each independently hydrogen, halo, hydroxy, $(C_1-C_6)$ alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, or $NR_cR_d$, with a phosphite of formula 39, wherein each R is independently a suitable radical (e.g. $(C_1-C_6)$alkyl, aryl, benzyl, or phenethyl, and preferably wherein each R is phenyl), yields an H-phosphate salt of formula 40 wherein ($M^+$) is a suitable counterion (e.g. triethylammonium); protection of the oxygen in compound 40 with a suitable protecting group "Pg" (e.g. a silyl protecting group such as trimethylsilyl or tert-butyldimethylsilyl) gives a compound of formula 41; treatment with iodine gives a highly reactive compound of formula 42, which can conveniently be reacted directly with an amino acid or peptide to give the nucleoside phosphoramidate of formula I.

Suitable protecting groups "Pg" are known in the art, for example see T. W. Greene, *Protecting Groups In Organic Synthesis*; Wiley: New York, 1981, and references cited therein. It may also be convenient to protect other functionalities in the intermediate compounds formulae 38-43 with suitable protecting groups that can be removed at a convenient point in the synthetic scheme.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Generally the phosphoramidate compounds of the invention are less toxic and have greater anti-cancer or anti-viral activity than the corresponding parent nucleosides. Additionally, phosphoramidates of the invention may be more soluable, more stable, have greater half-lives in vivo, or have better tissue distribution than the corresponding parent nucleosides.

The compounds of the invention can generally be prepared using procedures similar to those described in U.S. Pat. No. 6,475,985.

The ability of a compound of the invention to act as an antiviral agent may be determined using pharmacological models which are well known to the art, or using Test A or B described below.

Test A.

The antiviral activity of representative compounds of the invention was determined with matched HIV-1 isolates and a laboratory HIV-1 strain as previously described (D. L Mayers et al., *Proc. Natl. Acad. Sci.*, USA, 1995, 92, 215-219; and C. R. Wagner et al., *Bioorganic and Medicinal Chemistry Letters*, 1995, 5, 1819-1824).

Test B

The antiviral properties of compounds of the invention can also be determined in PBMCs using a procedure similar to that described by E. I. McIntee, et al. *J. Med. Chem.,* 1997, 40, 3323-3331.

The invention will now be illustrated by the following non-limiting Examples, wherein unless otherwise stated: NMR ($^1$H and $^{31}$P) spectra were recorded on Varian VXR-300 and GE Omega-300 spectrometers; an external standard of 85% $H_3PO_4$ was used for all $^{31}$P-NMR spectra; ESI mass spectra were obtained on a Finnigan TSQ 7000 mass spectrometer; analytical TLC was performed on Analtech Silica Gel GHLF (0.25 mm) or Machery-Nagel Polygram Sil G/UV$_{254}$ (0.2 mm) plates; concentration under reduced pressure refers to solvent removal on a Buchi rotary evaporator; high vacuum refers to <$10^{-2}$ psi attained with a DuoSeal mechanical pump; all solvents were reagent grade and used as received unless noted; and 3-deaza adenosine and 3-deaza aristeromycin (which can be prepared using procedures similar to those described by J. A. Montgomery, et al. *J. Med. Chem.,* 1982, 25, 626-629; and J. A. Montgomery, et al. *Heterocycl. Chem.,* 1977, 14, 195. were obtained from Walter Reed Army Institute of Research, Washington, D.C.

Test C

The anti-cancer properties of the compounds of the invention can be evaluated using the following assay.

CCRF-CEM cells were grown in medium containing RPMI 1640 supplemented with 10% heat-inactivated fetal bovine serum, penicillin (124 units/ml of medium) and streptomycin (0.125 mg/ml of medium). A stock solution of $10^5$ cells was made using Trypan Blue Dye Exclusion Method as a means of counting the cells. The following concentrations of test compounds were made: 250, 200, 100, 10, 1, 0.1, 0.01 and 0.001 µM. The cell stock (50 µl, 5×$10^4$ cells) was incubated with 50 µl of each of the compounds in triplicate in a 96-well plate. The cells were incubated with the compound at 37° C. in a 10% $CO_2$-90% air environment for 48 hr. A negative control was also done where the cells were incubated in drug-free medium.

Cell viability was determined by adding 20 µl of MTS reagent and incubating the cells for 4 hr after which the absorbance was found at 490 nm. Data for representative compounds is shown below.

| Compound | IC50 (µM) |
|---|---|
| 115 | 11 ± 14 |
| 113 | 229 ± 68 |
| 114 | 23 ± 7 |
| Ara-A | 384 ± 34 |

Example 1

Representative compounds of the invention can be prepared using a procedure similar to the one below.

Coupling of Ara-A 5'-monophosphate (1 eq) and amino acid methyl ester (1.1 eq) was carried out using EDC.HCl (5 eq) and N-methyl-morpholine (5 eq) buffered at pH=6.94. The reaction was monitored by silica TLC (5:3:0.5 CHCl$_3$:MeOH:H$_2$O). After completion, the reaction was concentrated and purified via silica column. The Ara-A phosphoramidate morpholine salt was passed through a Na+ exchange column to generate the sodium salt.

Example 2

Representative compounds of the invention can be prepared using a procedure similar to those described by T. Chou et al., *The Journal of Biological Chemistry*, 2005, 280, 15356-15361. The following compounds were prepared using such a procedure.

| Compound | Nucleotide | Amino Acid | Theoretical mass | [M − H]⁻ | Error (ppm) |
|---|---|---|---|---|---|
| 100 | AMP | L-TrpCOOMe | 546.1508 | 546.1503 | −0.9 |
| 101 | AMP | L-TrpCONMe | 547.1824 | 547.1851 | 4.9 |
| 102 | AMP | L-TrpCONH$_2$ | 533.1668 | 533.1669 | 0.3 |
| 103 | AMP | D-TrpCOOMe | 546.1508 | 546.1513 | 1.0 |
| 104 | AMP | Tryptamine | 488.1447 | 488.148 | 6.7 |
| 105 | GMP | L-TrpCOOMe | 562.1451 | 562.1468 | 3.0 |
| 106 | GMP | L-TrpCONMe | 563.1773 | 563.1813 | 7.1 |
| 107 | GMP | L-TrpCONH$_2$ | 547.146 | 547.1444 | −3.0 |
| 108 | GMP | D-TrpCOOMe | 562.1451 | 562.1462 | 1.9 |
| 109 | GMP | Tryptamine | 504.1397 | 504.140 | 0.7 |
| 110 | IMP | L-TrpCOOMe | 547.1342 | 547.1351 | 1.6 |
| 111 | IMP | D-TrpCOOMe | 547.1342 | 547.1335 | −1.4 |
| 112 | IMP | Tryptamine | 489.1288 | 489.1279 | −1.8 |
| 113 | Ara-AMP | L-TrpCOOMe | 546.1508 | 546.1496 | −2.1 |
| 114 | Ara-AMP | D-TrpCOOMe | 546.1508 | 546.1503 | −0.9 |
| 115 | Ara-AMP | Tryptamine | 488.1447 | 488.1422 | −5.2 |
| 116 | TMP | L-TrpCONMe | 520.1597 | 520.1592 | −1.0 |
| 117 | TMP | D-TrpCOOMe | 521.1437 | 521.1426 | −2.2 |
| 118 | TMP | Tryptamine | 463.1383 | 463.1396 | 2.9 |
| 119 | CMP | D-TrpCOOMe | 522.139 | 522.1399 | 1.7 |
| 120 | CMP | L-TrpCONH$_2$ | 507.1393 | 507.1399 | 1.1 |
| 121 | CMP | Tryptamine | 464.1335 | 464.1335 | 0.0 |
| 122 | UMP | D-TrpCOOMe | 523.123 | 523.124 | 1.9 |
| 123 | UMP | Tryptamine | 465.1175 | 465.1174 | −0.3 |

A = Adenosine, G = Guanosine, I = inosine, T = thymidine, U = uridine, Ara-A = 9-beta-D-arabinofuranosyladenosine Trp = tryptophan COOME = carbomethoxy ester, CONMe = methyl amide
*Most of compounds were analyzed in negative mode except compounds 101, 102, and 106.

Example 3

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula 1:

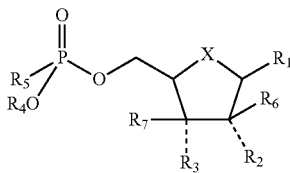

wherein:
R$_1$ is guanine, cytosine, thymine, 3-deazaadenine, or uracil;
R$_2$ is hydroxy;
R$_6$ is hydrogen or (C$_1$-C$_6$)alkyl;
R$_3$ is hydrogen, halo, hydroxy, (C$_1$-C$_6$)alkyl, (C$_3$-C$_6$)cycloalkyl, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, azido, cyano, N(R$_z$)C(=O)N(R$_{aa}$)(R$_{ab}$), —N(R$_z$)C(=O)OR$_{ac}$, or NR$_{ad}$R$_{ae}$;
R$_4$ is hydrogen, (C$_1$-C$_6$)alkyl, (C$_3$-C$_6$)cycloalkyl, aryl, aryl(C$_1$-C$_6$)alkyl, or 2-cyanoethyl;
R$_5$ is NR$_a$R$_b$;
R$_7$ is hydrogen, halo, hydroxy, (C$_1$-C$_6$)alkyl, (C$_3$-C$_6$)cycloalkyl, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, azido, cyano, —N(R$_z$)C(=O)N(R$_{aa}$)(R$_{ab}$), —N(R$_z$)C(=O)OR$_{ac}$, or NR$_{ad}$R$_{ae}$;
X is oxy, thio, or methylene;
each R$_a$ and R$_b$ is independently hydrogen, (C$_1$-C$_6$)alkyl, (C$_3$-C$_6$)cycloalkyl, aryl, or Het; or R$_a$ and R$_b$, together with the nitrogen to which they are attached form a nitrogen-linked Het;
each R$_w$ is independently hydrogen or (C$_1$-C$_6$)alkyl;
R$_x$ and R$_y$ are each independently hydrogen, (C$_1$-C$_6$)alkyl, (C$_3$-C$_6$)cycloalkyl, phenyl, benzyl, phenethyl, or (C$_1$-C$_6$)alkanoyl; or R$_x$ and R$_y$ together with the nitrogen to which they are attached are pyrrolidino, piperidino or morpholino;
R$_z$ is hydrogen, (C$_1$-C$_6$)alkyl, (C$_3$-C$_6$)cycloalkyl, phenyl, benzyl, or phenethyl;
R$_{aa}$ and R$_{ab}$ are each independently hydrogen, (C$_1$-C$_6$)alkyl, (C$_3$-C$_6$)cycloalkyl, phenyl, benzyl, or phenethyl; or R$_{aa}$ and R$_{ab}$ together with the nitrogen to which they are attached are pyrrolidino, piperidino or morpholino;
R$_{ac}$ is hydrogen, (C$_1$-C$_6$)alkyl, (C$_3$-C$_6$)cycloalkyl, phenyl, benzyl, or phenethyl;
R$_{ad}$ is hydrogen (C$_1$-C$_6$)alkyl, (C$_3$-C$_6$)cycloalkyl, phenyl, benzyl, or phenethyl;
R$_{ae}$ is hydrogen, (C$_1$-C$_6$)alkyl, (C$_3$-C$_6$)cycloalkyl, phenyl, benzyl, or phenethyl;
wherein any (C$_1$-C$_6$)alkyl of R$_1$-R$_7$, R$_w$, R$_x$, R$_y$, R$_z$, R$_{aa}$, R$_{ab}$, R$_{ac}$, R$_{ad}$, and R$_{ae}$ is optionally substituted with one or more halo, hydroxy, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, azido, cyano, oxo (=O), (C$_1$-C$_6$)alkyl, (C$_3$-C$_6$)cycloalkyl, (C$_3$-C$_6$)cycloalkyl(C$_1$-C$_6$)alkyl, (C$_1$-C$_6$)alkyl-S—(C$_1$-C$_6$)alkyl-, aryl, Het, aryl(C$_1$-C$_6$)alkyl, or Het(C$_1$-C$_6$)alkyl, or NR$_{aj}$R$_{ak}$; wherein each R$_{aj}$ and R$_{ak}$ is independently hydrogen, (C$_1$-C$_6$)alkyl, (C$_3$-C$_6$)cycloalkyl, phenyl, benzyl, or phenethyl;
wherein any (C$_1$-C$_6$)alkyl of R$_a$ and R$_b$ is optionally substituted with one or more halo, hydroxy, (C$_1$-C$_6$)alkoxy, (C$_3$-C$_6$)cycloalkyloxy, (C$_1$-C$_6$)alkanoyloxy, trifluoromethyl, azido, cyano, (C$_1$-C$_6$)alkyl, (C$_3$-C$_6$)cycloalkyl, (C$_3$-C$_6$)cycloalkyl(C$_1$-C$_6$)alkyl, (C$_1$-C$_6$)alkyl-S—(C$_1$-C$_6$)alkyl-, aryl, Het, aryl(C$_1$-C$_6$)alkyl, or Het(C$_1$-C$_6$)alkyl, or NR$_{aj}$R$_{ak}$; wherein each R$_{aj}$ and R$_{ak}$ is independently hydrogen, (C$_1$-C$_6$)alkyl, (C$_3$-C$_6$)cycloalkyl, phenyl, benzyl, or phenethyl;
and wherein any aryl or Het may optionally be substituted with one or more substituents selected from the group consisting of halo, hydroxy, (C$_1$-C$_6$)alkyl, (C$_3$-C$_6$)cycloalkyl, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, trifluoromethoxy, nitro, cyano, and amino;
or a pharmaceutically acceptable salt thereof.

2. The compound of claim 1 wherein R$_1$ is guanine.

3. The compound of claim 1 wherein R$_5$ is NR$_a$R$_b$, wherein R$_a$ is phenylmethyl and R$_b$ is hydrogen.

4. The compound of claim 1 wherein R$_a$ is (C$_1$-C$_6$)alkyl optionally substituted with one or more halo, hydroxy, (C$_1$-C$_6$)alkoxy, (C$_3$-C$_6$)cycloalkyloxy, (C$_1$-C$_6$)alkanoyloxy, trifluoromethyl, azido, cyano, (C$_1$-C$_6$)alkyl, (C$_3$-C$_6$)cycloalkyl, (C$_3$-C$_6$)cycloalkyl(C$_1$-C$_6$)alkyl, (C$_1$-C$_6$)alkyl-S—(C$_1$-C$_6$)alkyl-, aryl, Het, aryl(C$_1$-C$_6$)alkyl, or Het(C$_1$-C$_6$)alkyl, or NR$_{aj}$R$_{ak}$; wherein each R$_{aj}$ and R$_{ak}$ is independently hydrogen, (C$_1$-C$_6$)alkyl, (C$_3$-C$_6$)cycloalkyl, phenyl, benzyl, or phenethyl.

5. The compound of claim 1 wherein R$_a$ is (C$_1$-C$_6$)alkyl optionally substituted with one or more halo, hydroxy, (C$_1$-C$_6$)alkoxy, (C$_1$-C$_6$)alkanoyloxy, trifluoromethyl, cyano, aryl, or Het.

6. The compound of claim 1 wherein R$_a$ is (C$_1$-C$_6$)alkyl optionally substituted with one or more aryl or Het.

7. The compound of claim 6 wherein R$_a$ is (C$_1$-C$_6$)alkyl substituted with a phenyl, naphthyl, pyridyl, indolyl, isoindolyl, furyl, thienyl, pyrrolyl, benzofuranyl, benzothienyl, imidazolyl, thiazoyl, pyrrolidinyl, piperidinyl, piperazinyl, or morpholino ring, which ring is optionally substituted with one or more substituents selected from the group consisting of halo, hydroxy, (C$_1$-C$_6$)alkyl, (C$_3$-C$_6$)cycloalkyl, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, trifluoromethoxy, nitro, cyano, and amino.

8. The compound of claim 6 wherein R$_a$ is (C$_1$-C$_6$)alkyl substituted with a phenyl or indolyl ring, which ring is optionally substituted with one or more substituents selected from the group consisting of halo, hydroxy, (C$_1$-C$_6$)alkyl, (C$_3$-C$_6$)cycloalkyl, (C$_1$-C$_6$)alkoxy, (C$_3$-C$_6$)cycloalkyloxy, (C$_1$-C$_6$)alkanoyl, (C$_1$-C$_6$)alkanoyloxy, trifluoromethyl, trifluoromethoxy, nitro, cyano, and amino.

9. The compound of claim 6 wherein R$_a$ is (C$_1$-C$_6$)alkyl substituted with a phenyl ring.

10. The compound of claim 1 wherein R$_a$ is phenylmethyl, phenethyl, indolylmethyl, or 2-indolylethyl.

11. The compound of claim 1 wherein R$_b$ is hydrogen.

12. The compound of claim 1 wherein R$_3$ is hydroxy.

13. The compound of claim 1 wherein R$_4$ is methyl or ethyl.

14. The compound of claim 1 wherein R$_7$ is hydrogen or (C$_1$-C$_6$)alkyl.

15. The compound of claim 1 wherein:
R$_2$ is hydroxy;
R$_6$ is hydrogen or (C$_1$-C$_6$)alkyl;
R$_3$ is hydroxy;
R$_7$ is hydrogen or (C$_1$-C$_6$)alkyl;

$R_a$ is $(C_1-C_6)$alkyl substituted with a phenyl ring; and
$R_b$ is hydrogen.

16. The compound of claim 1 wherein any $(C_1-C_6)$alkyl of $R_1$-$R_7$, $R_a$, $R_b$, $R_w$, $R_x$, $R_y$, $R_z$, $R_{aa}$, $R_{ab}$, $R_{ac}$, $R_{ad}$, and $R_{ae}$ is optionally substituted with one or more halo, hydroxy, $(C_1$-$C_6)$alkoxy, $(C_3$-$C_6)$cycloalkyloxy, $(C_1$-$C_6)$alkanoyloxy, trifluoromethyl, azido, cyano, $(C_1$-$C_6)$alkyl, $(C_3$-$C_6)$cycloalkyl, $(C_3$-$C_6)$cycloalkyl$(C_1$-$C_6)$alkyl, $(C_1$-$C_6)$alkyl-S—$(C_1$-$C_6)$alkyl-, aryl, Het, aryl$(C_1$-$C_6)$alkyl, or Het$(C_1$-$C_6)$alkyl, or $NR_{aj}R_{ak}$; wherein each $R_{aj}$ and $R_{ak}$ is independently hydrogen, $(C_1$-$C_6)$alkyl, $(C_3$-$C_6)$cycloalkyl, phenyl, benzyl, or phenethyl.

\* \* \* \* \*

UNITED STATES PATENT AND TRADEMARK OFFICE
CERTIFICATE OF CORRECTION

PATENT NO.       : 8,765,935 B2                                    Page 1 of 1
APPLICATION NO.  : 13/753252
DATED            : July 1, 2014
INVENTOR(S)      : Carston R. Wagner It is certified that error appears in the above-identified patent and that said Letters Patent is hereby corrected as shown below:

In the Drawings

Figure 3:
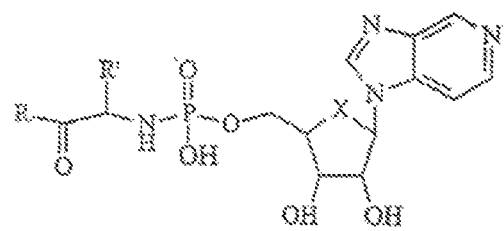
FIG. 3 Illustrates compounds useful in the methods of the invention.

Sheet 3 of 4, Fig. 3, delete " 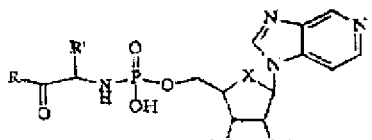 " and insert

-- 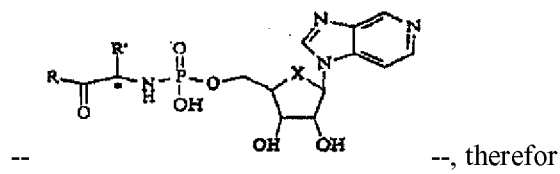  --, therefor

In the Specification

In column 15, line 21, delete "Ito" and insert --I to--, therefor

Signed and Sealed this
Thirtieth Day of September, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO.         : 8,765,935 B2
APPLICATION NO.    : 13/753252
DATED              : July 1, 2014
INVENTOR(S)        : Carston R. Wagner It is certified that error appears in the above-identified patent and that said Letters Patent is hereby corrected as shown below:

In the Specification

In column 1, lines 19-21, delete "The invention described herein was made with U.S. Government support under grant CA 89615 awarded by the National Institutes of Health, National Cancer Institute. The United States Government has certain rights in the invention." and insert -- This invention was made with government support under CA089615 awarded by the National Institutes of Health. The government has certain rights in the invention. --, therefor.

Signed and Sealed this
Twenty-second Day of December, 2015

Michelle K. Lee
*Director of the United States Patent and Trademark Office*